United States Patent
Feingold et al.

(10) Patent No.: US 9,459,415 B2
(45) Date of Patent: Oct. 4, 2016

(54) ENDOSCOPIC LED LIGHT SOURCE HAVING A FEEDBACK CONTROL SYSTEM

(75) Inventors: Benjamin Hyman Feingold, Mountain View, CA (US); Vasudev Nambakam, San Jose, CA (US); Simon S. Hui, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 227 days.

(21) Appl. No.: 12/998,375

(22) PCT Filed: Nov. 17, 2009

(86) PCT No.: PCT/US2009/006155
§ 371 (c)(1),
(2), (4) Date: Apr. 12, 2011

(87) PCT Pub. No.: WO2010/059197
PCT Pub. Date: May 27, 2010

(65) Prior Publication Data
US 2011/0208004 A1 Aug. 25, 2011

(51) Int. Cl.
*A61B 1/00* (2006.01)
*A61B 1/06* (2006.01)
(Continued)

(52) U.S. Cl.
CPC ......... *G02B 6/4215* (2013.01); *A61B 1/00006* (2013.01); *A61B 1/00126* (2013.01);
(Continued)

(58) Field of Classification Search
CPC .... A61B 319/52; A61B 3/13; A61B 1/0684; A61B 1/07; G02B 21/00; G02B 21/34; H05B 33/0833; H05B 33/0869
USPC ....... 600/178, 109, 101, 118, 476, 180, 182, 600/160, 167; 257/21; 348/65; 607/88; 362/321, 574; 396/17, 19
See application file for complete search history.

(56) References Cited

U.S. PATENT DOCUMENTS 4,538,062 A * 8/1985 Shishido ............... 250/201.4
5,084,612 A * 1/1992 Iwasaki et al. ............ 250/216
(Continued)

FOREIGN PATENT DOCUMENTS

CN   1870932 A   11/2006
CN  101295102 A   10/2008
(Continued)

OTHER PUBLICATIONS

International Search Report and Written Opinion dated Jun. 7, 2010 for corresponding PCT Application No. PCT/US2009/006155.
International Preliminary Report on Patentability and Written Opinion for corresponding PCT Application No. PCT/US2009/006155 dated Jun. 3, 2011.
First Office Action of Chinese Patent Office issued in Application No. 200980145842.3, date of issue Aug. 13, 2013 (13 pages), and English translation thereof.
(Continued)

*Primary Examiner* — Matthew J Kasztejna
*Assistant Examiner* — Aaron B Fairchild
(74) *Attorney, Agent, or Firm* — Flynn, Thiel, Boutell & Tanis, P.C.

(57) ABSTRACT

An external endoscope light source system includes light emitting diodes for providing a light output to an endoscope. The light is provided to a fiber optic cable for transmission to the endoscope. A fiber optic receives a portion of the light output and provides the output to a color sensor for sensing color values. The color values are provided to a controller that adjusts power to the various LEDs to provide a white light output. Instead of a color sensor in the light source, the light source can receive a white balance signal from a video camera provided for an endoscope. The white balance signal varies intensity of light output from each of the LEDs to obtain a white light output. The camera also provides shutter speed of a camera image sensor to the light source. The shutter speed is used to pulse or modulate the light output only when the shutter of the camera is open. By modulating the light output by the light source, the amount of heat generated by the light source is minimized.

2 Claims, 8 Drawing Sheets

(51) Int. Cl.
*A61B 1/07* (2006.01)
*A61B 1/045* (2006.01)
*G02B 6/42* (2006.01)
*A61B 1/12* (2006.01)
*F21V 8/00* (2006.01)
*G02B 6/293* (2006.01)

(52) U.S. Cl.
CPC ............. *A61B1/045* (2013.01); *A61B 1/0638* (2013.01); *A61B 1/0661* (2013.01); *A61B 1/0669* (2013.01); *A61B 1/0684* (2013.01); *A61B 1/07* (2013.01); *A61B 1/128* (2013.01); *G02B 6/0006* (2013.01); *G02B 6/4206* (2013.01); *G02B 6/4298* (2013.01); *G02B 6/29362* (2013.01); *G02B 6/4246* (2013.01)

(56) References Cited

U.S. PATENT DOCUMENTS

| | | | |
|---|---|---|---|
| 5,093,769 | A | 3/1992 | Luntsford |
| 5,132,526 | A * | 7/1992 | Iwasaki ................ 250/201.3 |
| 5,269,289 | A * | 12/1993 | Takehana et al. ............ 600/109 |
| 5,636,259 | A | 6/1997 | Khutoryansky et al. |
| 5,717,605 | A * | 2/1998 | Komiya et al. ............... 356/406 |
| 5,842,765 | A * | 12/1998 | Cassarly et al. ............... 362/21 |
| 5,917,883 | A | 6/1999 | Khutoryansky et al. |
| 5,957,834 | A * | 9/1999 | Mochida ................ 600/180 |
| 6,040,940 | A * | 3/2000 | Kawasaki ............... 359/389 |
| 6,193,401 | B1 * | 2/2001 | Girkin et al. .............. 362/551 |
| 6,485,414 | B1 * | 11/2002 | Neuberger ................. 600/182 |
| 6,549,239 | B1 * | 4/2003 | Tao ............... 348/371 |
| 6,563,632 | B1 * | 5/2003 | Schoeppe et al. ........... 359/368 |
| 6,663,560 | B2 * | 12/2003 | MacAulay et al. .......... 600/160 |
| 6,730,019 | B2 * | 5/2004 | Irion .................. 600/178 |
| 6,876,494 | B2 * | 4/2005 | Ishikawa et al. ............ 359/618 |
| 6,924,490 | B2 * | 8/2005 | Natori ........................ 250/458.1 |
| 7,015,444 | B2 * | 3/2006 | Kawano et al. ........... 250/201.3 |
| 7,016,053 | B2 * | 3/2006 | Moriuchi et al. ........... 356/601 |
| 7,176,428 | B2 * | 2/2007 | Kawano et al. ........... 250/201.3 |
| 7,223,986 | B2 * | 5/2007 | Natori ....................... 250/458.1 |
| 7,239,384 | B2 * | 7/2007 | Kawano ..................... 356/317 |
| 7,258,663 | B2 | 8/2007 | Doguchi et al. |
| 7,268,938 | B2 * | 9/2007 | Kawano et al. ............. 359/368 |
| 7,304,789 | B2 * | 12/2007 | Hirata et al. ............... 359/368 |
| 7,448,995 | B2 | 11/2008 | Wiklof et al. |
| 7,583,389 | B2 * | 9/2009 | Neal et al. ................... 356/512 |
| 7,609,440 | B2 * | 10/2009 | Tanikawa et al. ........... 359/368 |
| 7,616,330 | B2 * | 11/2009 | Neal et al. ................... 356/625 |
| 7,623,251 | B2 * | 11/2009 | Neal et al. ................... 356/625 |
| 7,661,862 | B2 | 2/2010 | Lee et al. |
| 8,408,704 | B2 * | 4/2013 | Tomidokoro et al. ........ 351/206 |
| 2002/0014595 | A1 * | 2/2002 | Sendai et al. ............. 250/458.1 |
| 2002/0043636 | A1 * | 4/2002 | Kimura ...................... 250/585 |
| 2002/0101643 | A1 * | 8/2002 | Kobayashi ................. 359/208 |
| 2002/0120181 | A1 * | 8/2002 | Irion .......................... 600/178 |
| 2002/0168096 | A1 * | 11/2002 | Hakamata et al. ........... 382/132 |
| 2003/0007087 | A1 | 1/2003 | Hakamata et al. |
| 2003/0042493 | A1 * | 3/2003 | Kazakevich ................ 257/98 |
| 2003/0067645 | A1 * | 4/2003 | Ibsen et al. ................. 359/124 |
| 2003/0147254 | A1 * | 8/2003 | Yoneda et al. .............. 362/551 |
| 2003/0169431 | A1 * | 9/2003 | Moriuchi et al. ............ 356/601 |
| 2003/0184661 | A1 * | 10/2003 | Yubata et al. .............. 348/229.1 |
| 2003/0202090 | A1 * | 10/2003 | Ota et al. ................... 348/69 |
| 2004/0061673 | A1 * | 4/2004 | Ishikawa et al. .............. 345/84 |
| 2004/0105095 | A1 * | 6/2004 | Stobrawa et al. ........... 356/318 |
| 2004/0105482 | A1 * | 6/2004 | Sugiyama et al. ........... 372/108 |
| 2004/0147806 | A1 * | 7/2004 | Adler ......................... 600/109 |
| 2004/0228373 | A1 * | 11/2004 | Tatsuno et al. ............. 372/29.02 |
| 2005/0020926 | A1 | 1/2005 | Wiklof et al. |
| 2005/0099824 | A1 * | 5/2005 | Dowling et al. ............. 362/572 |
| 2005/0187441 | A1 * | 8/2005 | Kawasaki et al. ........... 600/315 |
| 2005/0200947 | A1 * | 9/2005 | Hirata et al. ................ 359/368 |
| 2005/0203423 | A1 * | 9/2005 | Zeng et al. .................. 600/476 |
| 2005/0211872 | A1 * | 9/2005 | Kawano et al. ............ 250/201.3 |
| 2005/0224692 | A1 * | 10/2005 | Tsuchiya et al. ........... 250/201.3 |
| 2005/0228231 | A1 * | 10/2005 | MacKinnon et al. ........ 600/180 |
| 2005/0237604 | A1 * | 10/2005 | Kawano et al. .............. 359/368 |
| 2005/0251230 | A1 * | 11/2005 | MacKinnon et al. .......... 607/88 |
| 2005/0253056 | A1 * | 11/2005 | Nakata ......................... 250/234 |
| 2005/0270641 | A1 * | 12/2005 | Hirata et al. ................. 359/385 |
| 2005/0276553 | A1 * | 12/2005 | Kazakevich ................. 385/115 |
| 2005/0279950 | A1 * | 12/2005 | Kawano et al. ........... 250/458.1 |
| 2006/0009682 | A1 * | 1/2006 | Nagasawa et al. ........... 600/171 |
| 2006/0017920 | A1 * | 1/2006 | Tsuchiya et al. ............. 356/317 |
| 2006/0103922 | A1 * | 5/2006 | Tsuyuki ...................... 359/383 |
| 2006/0146125 | A1 * | 7/2006 | Yamada ........................ 348/51 |
| 2006/0175546 | A1 * | 8/2006 | Asai ........................... 250/234 |
| 2006/0187499 | A1 * | 8/2006 | Natori et al. ................. 358/474 |
| 2007/0028918 | A1 * | 2/2007 | Tsuyuki et al. .......... 128/203.12 |
| 2007/0051869 | A1 * | 3/2007 | Knebel ...................... 250/201.3 |
| 2007/0091425 | A1 * | 4/2007 | Kawano ...................... 359/385 |
| 2007/0097369 | A1 * | 5/2007 | Shimada ..................... 356/417 |
| 2007/0100241 | A1 * | 5/2007 | Adler .......................... 600/476 |
| 2007/0104417 | A1 * | 5/2007 | Tanaka et al. ................. 385/16 |
| 2007/0120070 | A1 * | 5/2007 | Kawano et al. ............ 250/458.1 |
| 2007/0153367 | A1 * | 7/2007 | Kawasaki .................... 359/368 |
| 2007/0159682 | A1 * | 7/2007 | Tanaka et al. ............... 359/320 |
| 2007/0188707 | A1 * | 8/2007 | Nanjo .......................... 351/206 |
| 2007/0213588 | A1 * | 9/2007 | Morishita et al. ............ 600/156 |
| 2007/0213593 | A1 * | 9/2007 | Nakaoka ..................... 600/181 |
| 2007/0236701 | A1 * | 10/2007 | Neal et al. ................... 356/512 |
| 2007/0236702 | A1 * | 10/2007 | Neal et al. ................... 356/512 |
| 2007/0236703 | A1 * | 10/2007 | Neal et al. ................... 356/512 |
| 2007/0270652 | A1 * | 11/2007 | Morishita et al. ............ 600/178 |
| 2007/0274649 | A1 * | 11/2007 | Takahashi et al. ........... 385/117 |
| 2007/0299309 | A1 * | 12/2007 | Seibel et al. ................. 600/117 |
| 2008/0039695 | A1 * | 2/2008 | Takaoka et al. .............. 600/178 |
| 2008/0043244 | A1 * | 2/2008 | Hatori et al. ................. 356/479 |
| 2008/0137328 | A1 | 6/2008 | Lee et al. |
| 2008/0186388 | A1 * | 8/2008 | Yamagata et al. .......... 348/222.1 |
| 2008/0198448 | A1 * | 8/2008 | Ganser et al. ............... 359/385 |
| 2008/0225388 | A1 * | 9/2008 | Hirata ......................... 359/385 |
| 2008/0232131 | A1 * | 9/2008 | Suda ........................... 362/574 |
| 2008/0246920 | A1 * | 10/2008 | Buczek et al. ............... 351/221 |
| 2008/0252900 | A1 * | 10/2008 | Hatori ......................... 356/482 |
| 2008/0283770 | A1 * | 11/2008 | Takahashi ................... 600/160 |
| 2009/0032732 | A1 * | 2/2009 | Konishi et al. ............ 250/458.1 |
| 2009/0067042 | A1 * | 3/2009 | Tanikawa et al. ........... 359/385 |
| 2009/0073553 | A1 * | 3/2009 | Hirata ......................... 359/383 |
| 2009/0201577 | A1 * | 8/2009 | LaPlante et al. ............ 359/355 |
| 2009/0244521 | A1 * | 10/2009 | Yazdanfar et al. .............. 356/73 |
| 2009/0251704 | A1 * | 10/2009 | Masuda ...................... 356/477 |
| 2012/0248333 | A1 * | 10/2012 | Fallert et al. .............. 250/458.1 |

FOREIGN PATENT DOCUMENTS

| | | | |
|---|---|---|---|
| EP | 1 930 751 | A2 | 6/2008 |
| JP | 54-10237 | Y2 | 6/1975 |
| JP | 7-67832 | A | 3/1995 |
| JP | 7-275192 | A | 10/1995 |
| JP | 11-253384 | A | 9/1999 |
| JP | 2001-224015 | A | 8/2001 |
| JP | 2006-087764 | | 4/2006 |
| WO | WO 2005/000110 | A2 | 1/2005 |

OTHER PUBLICATIONS

JP Office Action dated Jul. 19, 2013 and its English translation (7 pages).
Japanese Office Action issued in Appln. No. 2011-536337 with English translation dated Jul. 19, 2013 (7 pages).
Japanese Office Action issued in Appln. No. 2011-536337 with English translation dated Feb. 28, 2014 (6 pages).
Japanese Office Action issued in Appln. No. 2011-536337 with English translation dated Nov. 5, 2014 (5 pages).

* cited by examiner

ENDOSCOPIC LED LIGHT SOURCE HAVING A FEEDBACK CONTROL SYSTEM

CROSS REFERENCE TO RELATED APPLICATION

This application is the National Stage of International Application No. PCT/US2009/006155, filed Nov. 17, 2009, which claims the benefit of U.S. Provisional Application Ser. No. 61/199,597, filed Nov. 18, 2008, which is incorporated herein by reference in its entirety.

FIELD OF THE INVENTION

This invention relates to a solid-state system for providing illumination from an external light source through an endoscope to a surgical site. The external light source includes a fiber optic light cable providing light from the external source to an endoscope input.

BACKGROUND OF THE INVENTION

Light sources are used in endoscopy to inspect regions within a body during surgery. Typically, an endoscope includes a rigid or flexible elongate insertion tube equipped with a set of optical fibers that extend from a proximal handle through the endoscope body to a distal viewing tip thereof. An external light source provides light to the optic fibers via a cable that attaches to a post on a side of the endoscope. In some embodiments, the endoscope includes an imaging device for providing a image to a monitor for viewing by a surgeon.

Prior art FIGS. 1 and 2 are taken from U.S. Pat. No. 6,921,920, which discloses a solid state light source. As illustrated in FIG. 1, an endoscopic system 10 for providing illumination can include a solid-state light source 12, a video monitor 14, a camera 16, and endoscope 18. The light source 12 generates white light that is conveyed to a distal end 22 of the endoscope 18 via a light guide 26. The light guide 26 includes multiple fibers and is connected between an output connector 28 of the light source 12 and a light post 30 of the endoscope 18. The white light illuminates a working area 24 at the distal end 22 of the endoscope. The video camera 16, connected to a handle 32 of the endoscope generates video signals representative of images at the working area 24 for display on video monitor 14.

FIG. 2 shows a schematic of a specific light source 12 for the known arrangement of FIG. 1. The light source 12 of FIG. 2 includes an optical system 34 and a lens array 36 used to collimate light from a corresponding LED array 38. A focusing lens 40 then focuses the light onto a light guide 52.

LED array 38 is arranged in a circular-shaped 2-dimensional array. Corresponding lens array 36 is located in front of the LED array 38 so that each semi-conductor light source 42 is positioned along an optical axis 44 of the corresponding lens 46. Lenses 46 collimate light emitted by their corresponding LEDs 42. Lenses 46 may represent single lenses, such as single or double aspherics, compound lenses, radiant index type lenses or combinations of each. Other arrangements have lens arrays that are implemented as part of an LED array by adhesion, fusion or the like. Some arrangements have a rectangular shaped LED and lens array.

The focal length of the lens 40, and the diameter of the lenses 46 are chosen on the order of a few millimeters. The actual values are selected based on the size of LED emitting surface 48 which determines the field of view of the lens 46.

The collimated light from lens array 36 travels to the focusing lens 40. Focusing lens 40 projects the image of each LED light emitting surface 48 onto an entrance face 50 of the light guide 42. The image is magnified so that the size is approximately equal to the size of the entrance face 50 of the light guide 42. The light guide 42 transports the light to an endoscope. The light passes through the endoscope to illuminate a surgical site. Camera 16 provides images of the surgical site for display on video monitor 14.

An area of concern with the above described endoscopic system and other endoscopic illuminating systems is the transfer of heat from a light source through the light guide 26 to a metal junction at the distal end of the scope. In some instances, the temperature at the distal end of the scope can be as high as 70° C. If a surgeon removes the endoscope from within a patient and places the endoscope on their body, burning of the skin of a patient may occur. Further, when the endoscope is disposed inside the body of a user, there is a possibility that the metal distal tip will injure tissue of the patient.

One object of the invention is to provide an apparatus having a plurality of solid state light sources that are operated at a minimal voltage or power level while providing a necessary amount of light.

One embodiment of the invention is to sense the color of light applied through an endoscope to the surgical site. Depending on the sensed color values, the power to individual light emitting diodes or diode arrays is controlled to balance the colors of light to result in a white light. In this way, white balance in a camera receiving reflected light from the light source is not as necessary as compared to light sources having no color balance feedback.

Another embodiment of the invention automatically stops providing power to the light source when the distal end of the fiber optic cable is disconnected from the endoscope.

Figure 1:
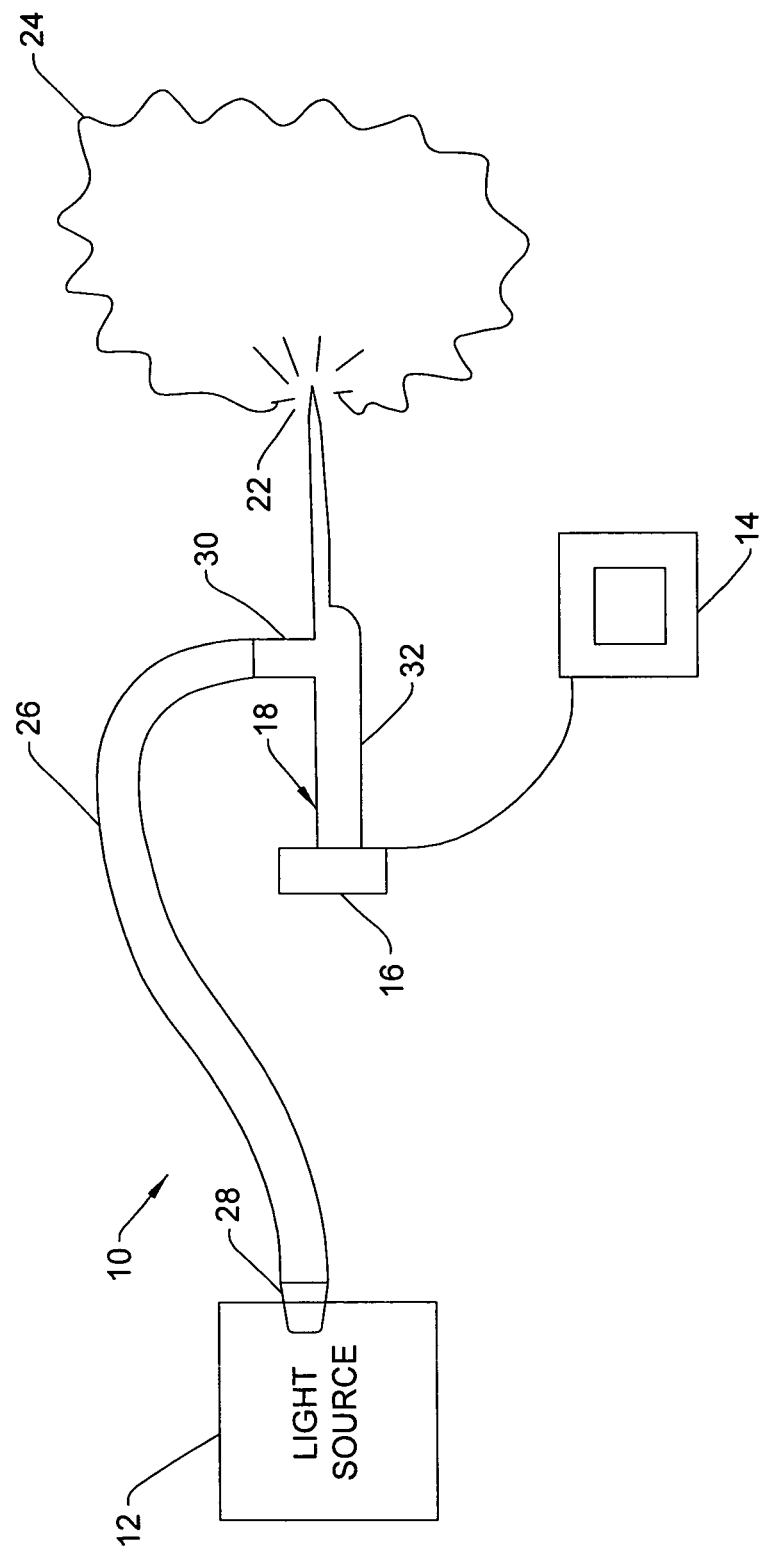
FIG. 1 is a drawing of a known endoscope system.
Figure 2:
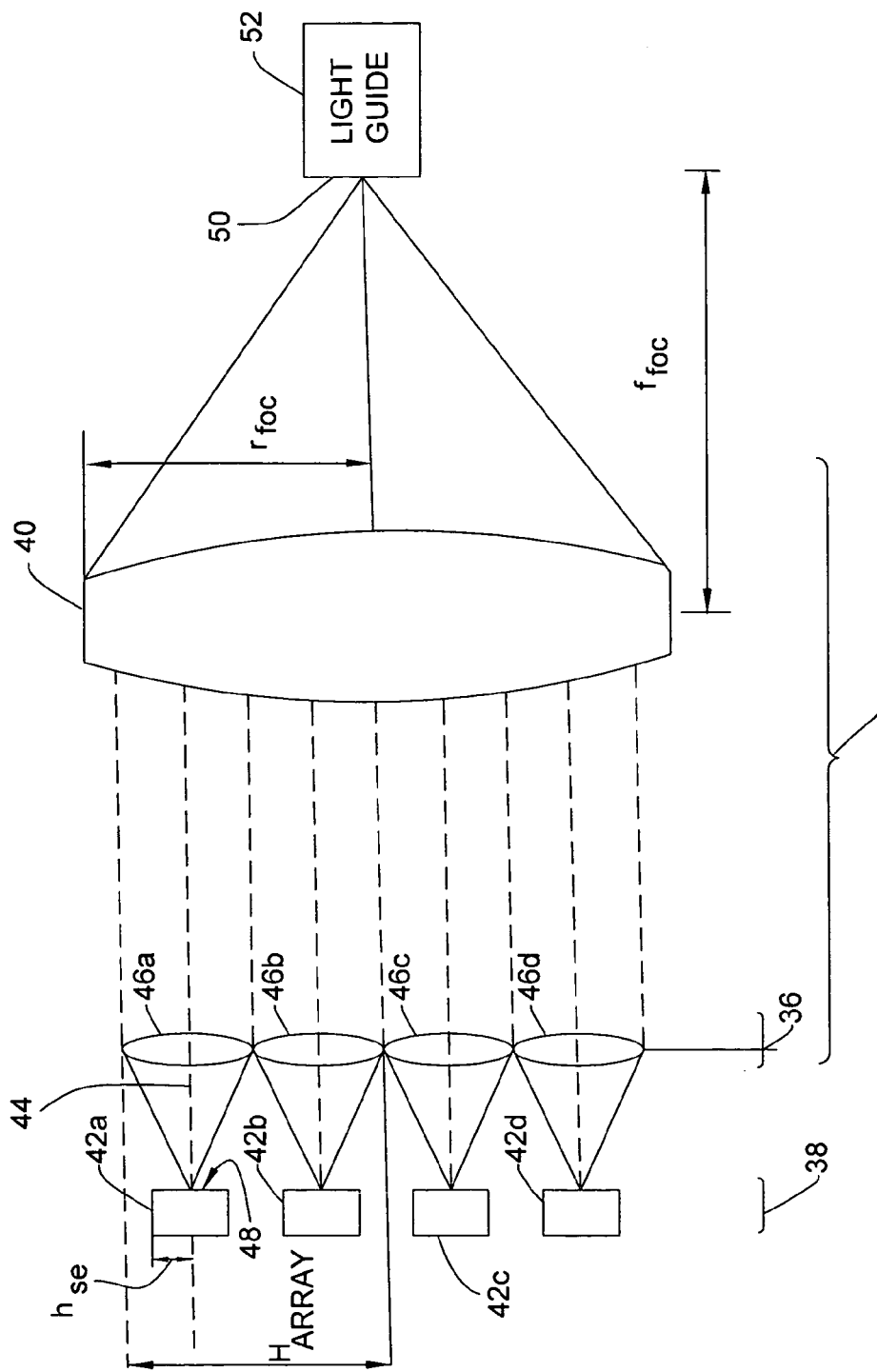
FIG. 2 is an optical system for the endoscope system of FIG. 1.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement, and designated parts thereof. Said terminology will include the words specifically mentioned, derivatives thereof, and words of similar import.

DETAILED DESCRIPTION

Figure 3:
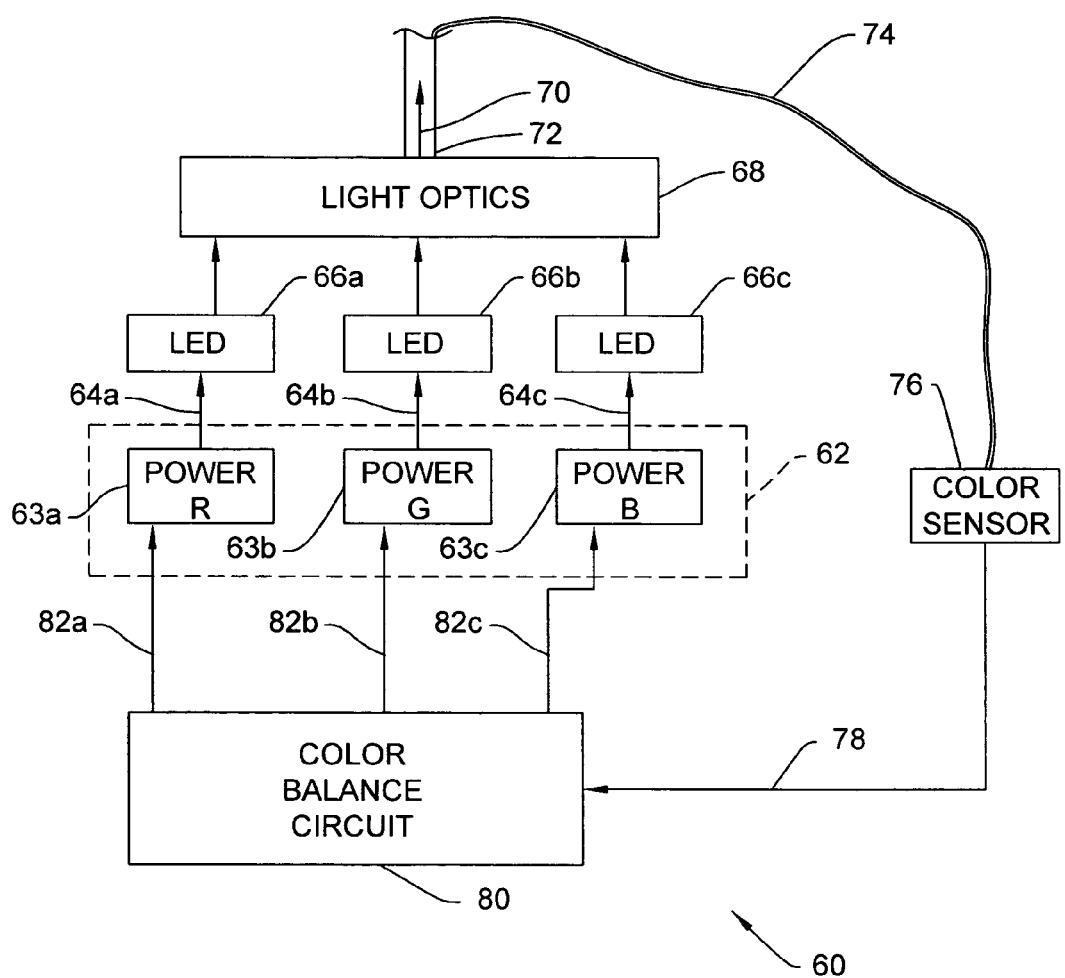
FIG. 3 is a block diagram of a first light source embodiment of the invention.

FIG. 3 is a block diagram of a light source 60 including a power supply unit 62 that provides a plurality of power outputs 64a, 64b, 64c to solid state light emitting devices, such as light emitting diodes 66a, 66b, 66c. The light emitting diodes 66a-66c provide light to light optics 68 which will be described in more detail below. Light optics 68 provide a collimated light output 70 to and within a hollow light transmitting rod 72. The light output 70 is intended to be white light.

At a distal end of the light transmitting rod 72, a fiber optic 74 is oriented to receive a miniscule portion of the light output 70. The fiber optic 74 provides the light received therein to a color sensor 76 disposed in the light source housing. The color sensor 76 provides a color output signal 78 to a color balance circuit 80. The color balance circuit provides color balance output signals 82a, 82b, 82c to the power supply unit 62. The power supply unit 62 includes individual power output circuits 63a-63c that supply power to LEDs or LED arrays 66a-66c.

In operation, the light source embodiment illustrated in FIG. 3 provides a light output 70 to light transmitting rod 72 that is received by a fiber optic cable that provides the light output to an endoscope.

In addition to the light output 70 for an endoscope, fiber optic 74 disposed at an edge at the distal end of the rod 72 receives a small portion of the light output 72 and provides the light to the color sensor 76. The color sensor 76 senses the properties of the light and determines what, if any, colors are dominant within the light output 70. For example, if an abundance of red light is provided in the light output 70, the condition will change the complexion or color of an image of an object on which the light output is reflected. Thus, color sensor 76 receives light from fiber optic 74 and determines the intensity of color in the fiber optic 74. Then, color sensor 76 provides color output signals 78 corresponding to combined light from the LEDs or solid state light emitting elements 66.

Color balance circuit 80 receives the color output signals 78 from the color sensor 76 and determines which, if any, of the colored light emitting diodes 66a-66c needs to output more or less light to the fiber optics 68. The color balance circuit 80 then provides color balance output signals 82a, 82b, 82c to the power supply unit 62. Power output circuits 63a-63c individually control the light emitting diodes 66a-66c based on the color balance output signals 82 to obtain, in accordance with one embodiment, a balanced white light output 70. However, in some situations, a white light output may not be the most ideal light color for viewing an operating field. Thus, the color balance circuit 80 operates to control the light emitting elements to provide the predetermined desired color.

In conclusion, the light source arrangement shown in FIG. 3, which is contained within a light source housing, operates to provide a predetermined color light output 70, regardless of the conditions or properties of the various individual light emitting diodes 66a-66c which provide the light that is processed and output through the light transmitting rod 72.

Light Optics

Figure 4:
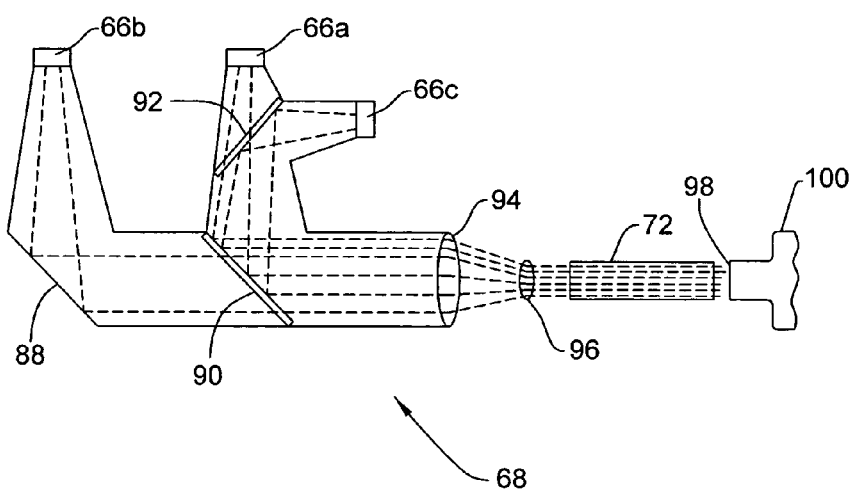
FIG. 4 is a light optic for one embodiment of the light source.

FIG. 4 illustrates one embodiment of the light optics 68 provided within light source 60. The FIG. 4 embodiment includes red, green and blue LEDs 66a-66c, respectively.

The light optics 68 include a plurality of walls for containing light provided by the respective LEDs 66a-66c.

The light optics 68 include a reflector or mirror 88 disposed below the green LED 66b for reflecting green light. The reflector 88 is oriented at approximately a 45 degree angle to reflect the green light in a substantially transverse horizontal direction as illustrated in FIG. 4. The green light is reflected toward a first dichroic band pass filter 90 that allows green light to pass therethrough.

In FIG. 4, red LED 66a provides red light that is directed downwardly and passes through a second angled high-pass dichroic filter 92. The dichroic filters 90 and 92 are glass filters with dichroic coatings. After passing through the dichroic filter 92, the red light advances to the first band pass filter 90 and is reflected transversely therefrom and substantially into alignment with the green light passing through the filter 90. Thus, the red light and the green light travel along the same optical path.

Blue LED 66c provides light along a path transverse to the direction of light from red LED 66a. The blue light reflects downwardly from a surface the high-pass dichroic filter 92 in the same direction and along the same path as the red light. The blue light then reflects, along with the red light, from the surface of the band pass dichroic filter 90 transversely, and in substantially the same direction as the green light.

The combined red, blue and green light passes through a focusing lens 94 that narrows the optic path of the combined light and then passes through a collimating lens 96 for entry into the light transmitting rod 72.

The light transmitting rod 72 can be a glass rod that is adapted for connection to a proximal end 98 of a fiber optic cable 100. Thus, the light optics 68 combine a plurality of colors to obtain a white light output 70 for transfer to a fiber optic cable 100. In some embodiments, the fiber optic cable 100 includes a plurality of optical fibers extending along the length thereof.

Figure 5:
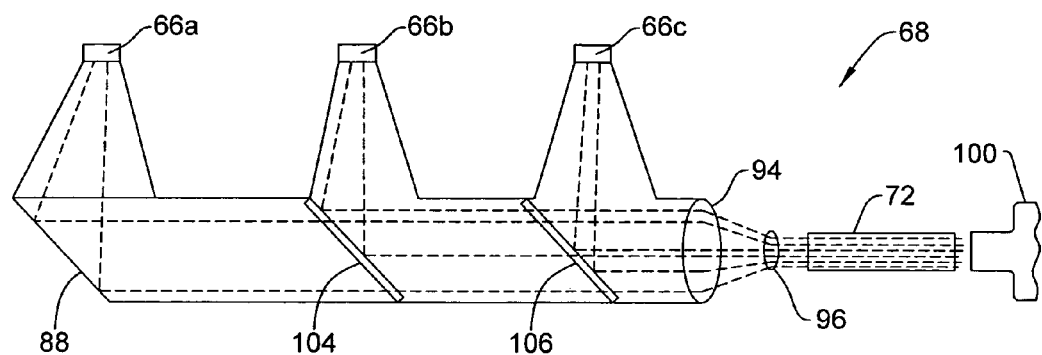
FIG. 5 is a light optic of another embodiment of the light source.

FIG. 5 is another embodiment of the light optics 68 that differs from the embodiment shown in FIG. 4. In FIG. 5, the LEDs 66a-66c are all positioned transverse to an optical output path of the light optics 68.

Red LED 66a provides light that is reflected transversely by an angled reflector or mirror 88. The red light travels along an optical path and passes through an angled high-pass filter 104. Green LED 66b provides light in a parallel downward path that is reflected transversely by the high-pass dichroic filter 104. The dichroic filter 104 is oriented at approximately a 45° angle so that the red and green light combine and travel along essentially the same optical path.

The blue LED 66c also outputs light in a downward direction that is reflected transversely by an angled high-pass dichroic filter 106. The dichroic filter 106 allows the red and green light to pass therethrough along the same optical path as the blue light.

The red, blue and green light are combined along a single optical path and travel to a focusing lens 94. The focusing lens 94 focuses the combined light and directs the light to a collimating lens 96. The collimating lens 96 orients the light in a straight direction for entry into the receiving rod 72. As discussed above, the receiving rod 72 transfers light to the proximal end 98 of a fiber optic cable 100. The proximal end 98 of the fiber optic cable 100 inserts into a light source housing that contains the light transmitting rod 72. The rod 72 is oriented so that the distal end thereof opens through a housing wall to receive the proximal end 98 of the fiber optic cable 100.

Light Source Controlled by Inputs from Camera

Figure 6:
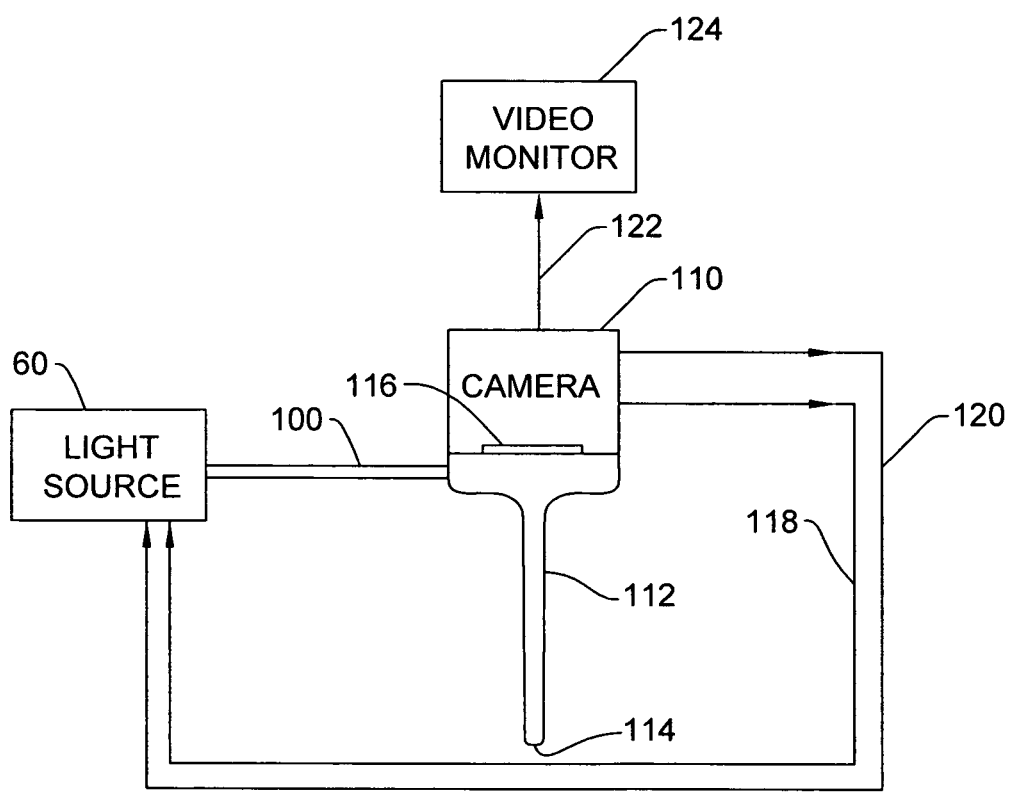
FIG. 6 is a block diagram of another embodiment including a light source in combination with an endoscopic camera.

The block diagram of FIG. 6 shows another embodiment of the invention wherein the light source 60 is controlled by feedback signals from a camera 110. The proximal end 98 of the fiber optic cable 100 connects to the light source 60 as discussed above, and a distal end of the fiber optic cable connects to a light receiving port of an endoscope 112. The endoscope has an optical path therein to project the white light output received at the port outwardly from a distal end 114 thereof. A reflected image is then provided to an image sensor 116 of the camera 110 disposed at a proximal end of the endoscope 112.

As will be discussed in more detail below, the camera 110 outputs one or both of a color balance signal 118 and a shutter speed signal 120. The color signal 118 and the shutter speed signal 120 are provided as control signals to the light source 60. In FIG. 6, an image received by the camera 110 is also provided as an image output 122 and displayed on a video monitor 124.

Figure 7:
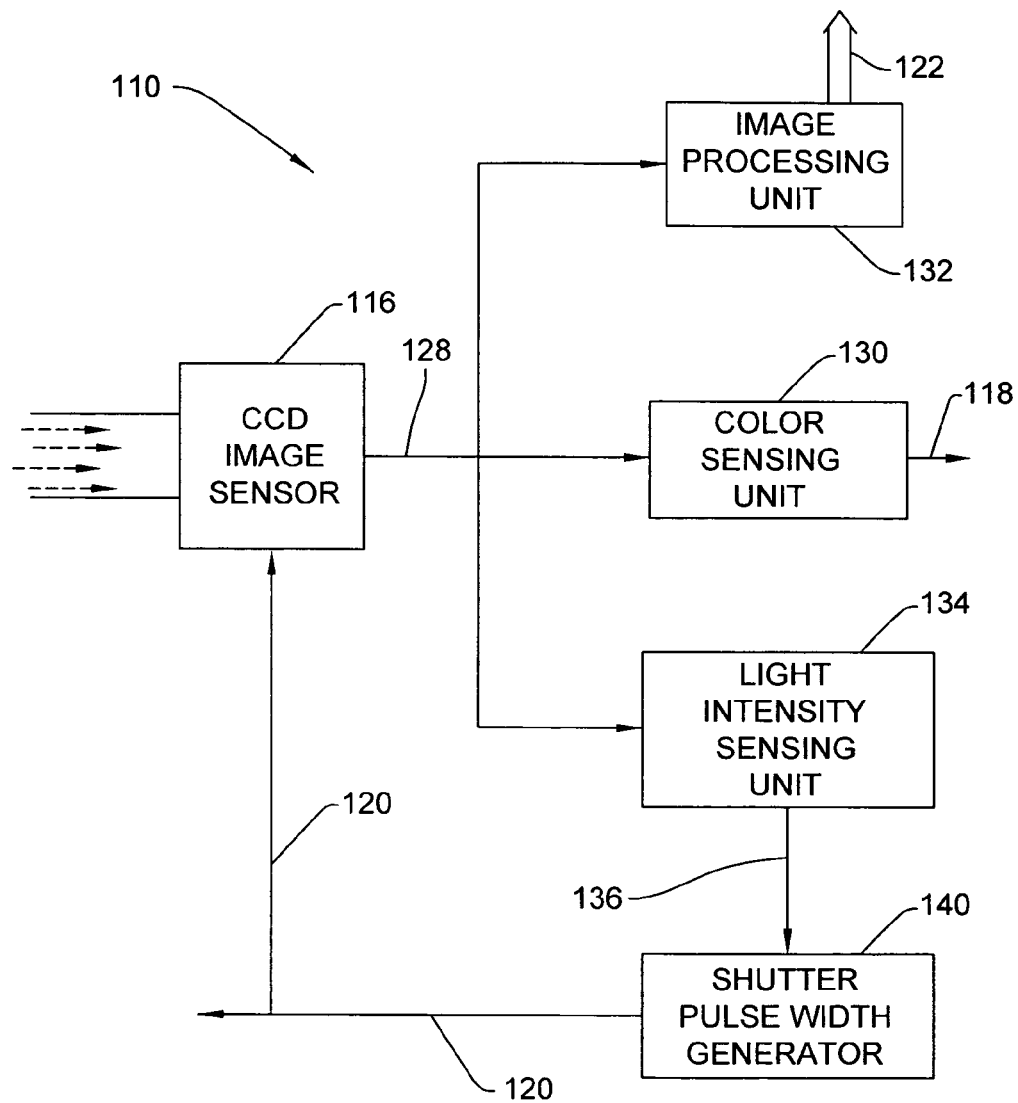
FIG. 7 is a block diagram of the light source in FIG. 6.

The block diagram of camera 110 illustrated in FIG. 7 is provided for the purpose of showing processing details for providing the signals 118, 120 to the light source 60. The diagram is not intended to represent a detailed operation of the camera 110 or structural elements of the camera. Thus, various units 122, 130, 134, 140 shown in the block diagram of FIG. 7 may be provided as operations conducted by a single processor.

The camera 110 is intended to be a high definition digital camera having, for example, a 60 frames per second imaging rate, and having the capability of adjusting the shutter speed for the respective frames.

The image sensor 116 shown in FIG. 7, senses an image from a surgical site and provides a sensed image signal 128 to the processing units 130, 132, 134 of the camera 110.

Color sensing element 130 receives the image signal 128 and determines the white balance of the image and what, if any, colors are detracting from the desired predetermined color light output, which typically is white light. The color sensing element 130 then outputs a color balance signal 118 containing the measured color information.

Image processing unit 132 also receives the image signal 128 and provides an image output 122 to the video monitor 124 for display thereon in a standard manner.

Light intensity sensing unit 134 also receives the image signal 128. The light intensity sensing unit 134 determines the brightness of the image and thus the required shutter speed for the image sensor 116. The light intensity sensing unit 134 provides an intensity feedback signal 136 to a shutter pulse width generator 140.

The shutter pulse width generator 140 provides a shutter speed signal 120 to the image sensor 116 to control the shutter speed thereof. The shutter speed is increased in time (length of time open) when more light needs to be sensed and the shutter speed is decreased in time when a bright light image is input to the image sensor 116. This brightness control operation is generally provided in digital video cameras.

Light Source

Light source 60 illustrated in the block diagram of FIG. 8 cooperates with the input signals 118, 120 received from the camera 110 (illustrated in FIG. 7) as follows. Color balance signal 118 from the camera 110 is received by a color balance circuit 148 of the light source 60. Shutter speed signal 120 from the camera is received by a pulse width generator 150 of the light source 60. The pulse width generator 150 provides output signals 151 to a light source power unit 152. The light source power unit 152 also receives a plurality of color balance outputs 156a-156c from the color balance circuit 148.

The light source power unit 152 includes individual power supply output circuits 160a, 160b, 160c that receive the respective color balance outputs 156a-156c and includes the pulse width generator output 151 from the pulse width generator 150.

The power supply output circuits 160a-160c connect to respective LEDs 66a-66c, which provide light to the light optics 68 in a manner described above with respect to FIGS. 3-5. As shown in FIG. 3, the light optics provide a light output 70 to a fiber optic cable 100.

In operation, as discussed above, the camera 110 determines a color balance signal 118 and determines a shutter speed signal 120. The signals 118, 120 are provided to the light source 60.

As described with respect to FIG. 3, the color balance signal 118 is processed by the color balance circuit 148 to provide color balance outputs 156a-156c to the power supply circuits 160a-160c resulting in a predetermined color light output. The color adjustment accounts for any needed changes in intensity of the individual colors of light provided by LEDs 66a-66c.

Modulation

Figure 8:
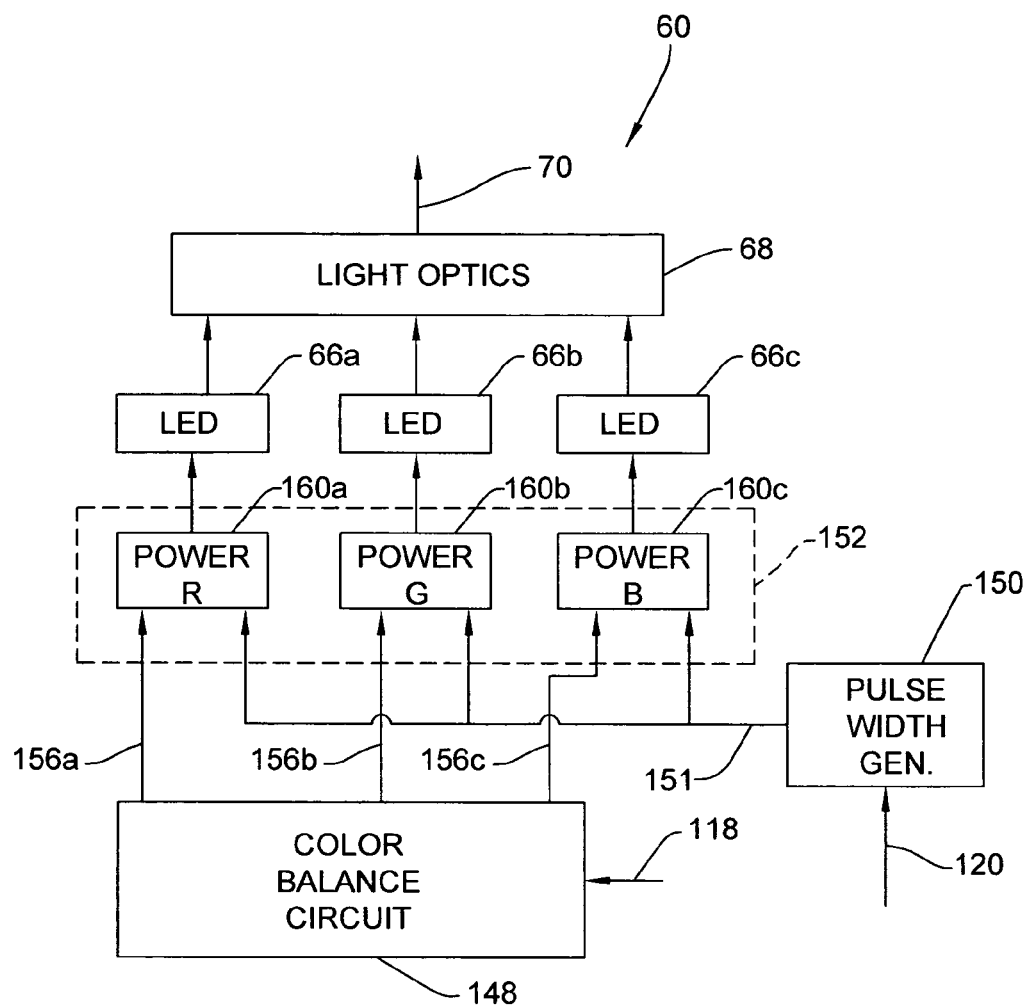
FIG. 8 is a block diagram of the endoscopic camera in FIG. 6.

The light output 70 of the light optics 68 illustrated in FIG. 8 is modulated in accordance with the shutter speed of the image sensor 116 of the camera. Thus, the LEDs 66a-66c are modulated to periodically provide the light output 70.

In operation, the shutter speed signal 120 is received by pulse width generator 150 of the light source 60. The pulse width generator 150 provides pulses 151 having a width to control the amount of time the LEDs 66a-66c output light during each frame of image sensor operation of the camera 110.

For instance, if the camera 110 requires a slower shutter speed, light must be output by the light source power unit 152 to the LEDs 66a-66c for a longer period of time. Thus, the feedback arrangement is balanced so that the light output 70 of the light source enables the image sensor 116 to operate at a predetermined shutter speed or within a predetermined desired range of shutter speeds. The LEDs 66a-66c must pulse in synchronism with the camera shutter speed to provide adequate light output 70 while using less power.

In some embodiments, the predetermined range of shutter speeds are chosen to minimize the intensity or the time period of the light output 70 from the light source 60. Minimizing the length of time for light output 70, while maintaining a desired image output 122 for the camera 110, reduces heat generated at the distal end 114 of the endoscope 112 by the passage of light from the light source 60 therethrough. Further, minimizing the intensity of the light output 70 also reduces the amount of heat generated by the light at the distal end 114 of the endoscope 112. Therefore, in this arrangement with feedback control, the image sensor 116 preferably operates at the fastest acceptable shutter speed in order to reduce the intensity and/or modulation period of light provided to the image sensor 116.

In some embodiments, only the shutter speed signal 120 having a predetermined pulse width is provided to the light source 60 to modulate the light output 70.

In some embodiments, only the color balance signal 118 is provided to the light source 60 for controlling the light output from each of the LEDs 66a-66c. Finally, in another embodiment (not shown), the light intensity feedback signal 136 is provided to the light source 60 to control only the intensity of light emitted therefrom.

In some embodiments the system compensates for the target distance of an organ or tissue from the image sensor 116 at the surgical site. For example, the greater the distance of the target from the image sensor 116, the greater the intensity for the light output 70 to provide for optimal viewing.

Alternatives

While the embodiments of FIGS. 3-8 show the LEDs 66 as three LEDs defined by a red LED 66*a*, a green LED 66*b* and a blue LED 66*c*, other embodiments are contemplated. First, rather than individual LEDs, each of the LEDs may be defined by an array of LEDs or other solid-state devices.

Other embodiments may include cyan, magenta and amber LEDs. Further, any combination of one or more of red, green, blue, cyan, magenta and amber LEDs is contemplated. In some embodiments, the light output may be generated by white LEDs or a combination of white and red LEDs. Finally, in yet another embodiment, a white light output 70 is generated by blue LEDs coated with yellow phosphorous.

In some embodiments, the light transmitting rod 72 of the light source 60 has a rectangular shape for coupling to a proximal end 98 of the fiber optic cable 100, which also has a rectangular shape. This arrangement provides a more efficient light transmission path between the light transmitting rod 72, and the fiber optic cable 100, since the LED geometry of the light source 60 is rectangular.

Automatic Light Source Shut Off

Figure 9:
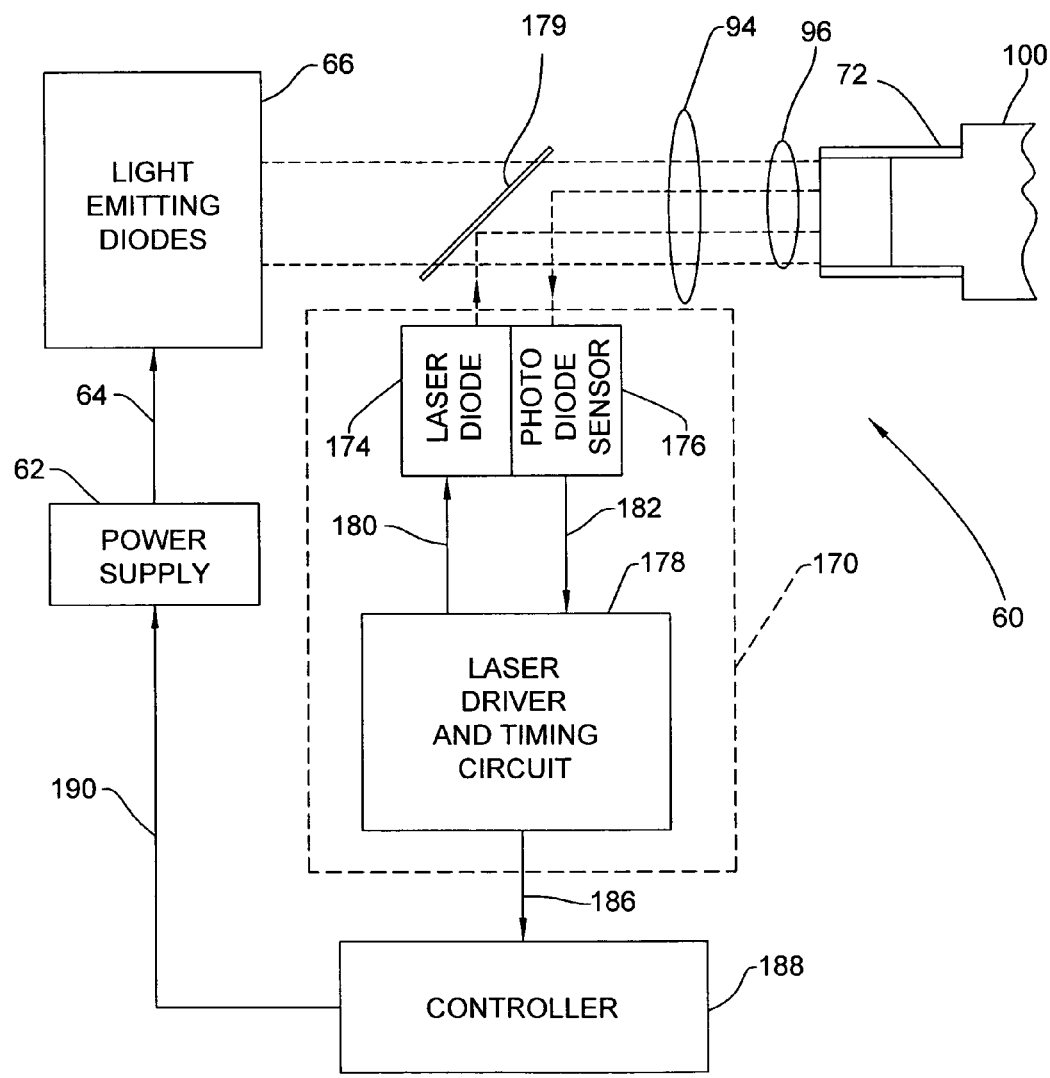
FIG. 9 is a block diagram of a light source having a fiber optic cable presence sensor for determining whether the cable is connected to an endoscope.

The FIG. 9 embodiment of the invention includes an arrangement to detect when the distal end of the fiber optic cable 100 is detached from the port of the endoscope 112. When the distal end of the fiber optic cable 100 is detached, the light source 60 automatically shuts down to minimize the amount of light and heat energy output by the light source 60, and thus the amount of light/heat provided along the fiber optic cable 100 and through the endoscope 112 to the distal end 114 thereof. The distal end 114 of the endoscope 112 may have a metal structure or elements that can become overheated.

The light source 60 illustrated in FIG. 9 includes a fiber optic cable disconnection detecting unit 170 for determining when the distal end of the fiber optic cable 100 is detached from the endoscope 112. The cable disconnection detecting unit 170 includes a laser output diode 174 and a photodiode sensor 176. A laser driver and timing circuit 178, periodically provides a laser diode drive output 180 to the laser diode 174. After a laser pulse or signal is output by the laser diode 174, the laser pulse is reflected by dichroic filter 179 and passes through the focusing lens 94 and the collimating lens 96 to the fiber optic cable 100. The laser light passes along the fiber optic cable 100 to the distal end thereof. If the distal end of the fiber optic cable 100 is not connected to the endoscope 112, the laser pulse reflects at the open distal end and travels back through the fiber optic cable 100, the lenses 94, 96 and reflects off the dichroic filter 179.

The laser pulse is then detected by the photodiode sensor 176, which provides a laser pulse reflection signal 182 to the laser driver and timing circuit 178. The laser driver and timing circuit 178 determines the length of time for the laser pulse to return to the detecting unit 170 and then provides a timing output value 186 to controller 188.

The controller 188 is programmed with the physical length of the fiber optic cable 100 and compares the length of time of the timing output value 186 with a time value range corresponding to the known length for the fiber optic cable 100. If the time length signal values are within the predetermined range for the expected reflection time, the controller 188 outputs a disconnect or power shutdown signal 190 to the power supply 62, which turns off the power supply so that no power output 64 is provided to the LEDs 66. Therefore, upon disconnection of the fiber optic cable 100 from the endoscope 112, light and heat no longer are output by the light source 60 or transmitted to the endoscope.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. An external endoscopic light source system comprising:
    a plurality of light emitting diodes, each light emitting diode capable of producing a different illumination color with respect to at least one of the other light emitting diodes;
    a plurality of dichroic filter elements for receiving light from the light emitting diodes;
    a light collimating and mixing device for receiving light from the dichroic filter elements;
    an image sensor for sensing an image from a surgical site;
    an interface connected to a fiber optic cable such that the fiber optic cable can receive light from the light collimating and mixing device;
    a color sensor for sensing a color value from the illumination in a light path, the fiber optic cable comprising a plurality of optical fibers, and one of said optical fibers directly providing light to said color sensor;
    a controller for receiving the color value from the color sensor and comparing the color value with a predetermined color value; and
    a camera control unit for determining the amount of light received by the image sensor and providing an intensity feedback signal to a generator, the generator providing a shutter speed signal which results in a fast shutter opening time for the camera when receiving bright light and a slower shutter opening time when receiving dim light at a surgical site, wherein the shutter opening time results in an image having desired light characteristics;
    wherein the controller is capable of varying a power signal to control the light intensity output by at least one of the plurality of light emitting diodes based on signals from the color sensor and the generator, so that the color illumination from the light emitting diodes is balanced according to a predetermined balance level and the color value sensed by the color sensor corresponds to a predetermined color light output.

2. The endoscopic light source system according to claim 1, wherein said color sensor is positioned within a light source housing.

* * * * *

UNITED STATES PATENT AND TRADEMARK OFFICE
CERTIFICATE OF CORRECTION

| | |
|---|---|
| PATENT NO. | : 9,459,415 B2 |
| APPLICATION NO. | : 12/998375 |
| DATED | : October 4, 2016 |
| INVENTOR(S) | : Benjamin Hyman Feingold et al. |

It is certified that error appears in the above-identified patent and that said Letters Patent is hereby corrected as shown below:

On the title page, the "Related U.S. Application Data" is missing. Please insert item (60) to read as follows:

--(60) Provisional Application No. 61/199,597, filed on November 18, 2008.--

Signed and Sealed this
Sixth Day of December, 2016

Michelle K. Lee
*Director of the United States Patent and Trademark Office*